United States Patent
Abbas et al.

(10) Patent No.: US 10,577,580 B2
(45) Date of Patent: Mar. 3, 2020

(54) **METHODS FOR THE POSITIVE SELECTION OF ETHANOL OVERPRODUCING MUTANTS FROM *SACCHAROMYCES CEREVISIAE***

(71) Applicant: Archer Daniels Midland Company, Decatur, IL (US)

(72) Inventors: Charles A Abbas, Champaign, IL (US); Andriy Sibirny, Lviv (UA); Kostyantyn Dmytruk, Lviv (UA); Barbara Kshanovska, Lviv (UA)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 3 days.

(21) Appl. No.: 15/572,385

(22) PCT Filed: Mar. 30, 2016

(86) PCT No.: PCT/US2016/024910
§ 371 (c)(1),
(2) Date: Nov. 7, 2017

(87) PCT Pub. No.: WO2016/164223
PCT Pub. Date: Oct. 13, 2016

(65) Prior Publication Data
US 2018/0127708 A1  May 10, 2018

Related U.S. Application Data

(60) Provisional application No. 62/145,606, filed on Apr. 10, 2015.

(51) Int. Cl.
*C12N 15/01* (2006.01)
*C12N 1/18* (2006.01)
*C12P 7/06* (2006.01)
*C12R 1/865* (2006.01)

(52) U.S. Cl.
CPC ............... *C12N 1/18* (2013.01); *C12N 15/01* (2013.01); *C12P 7/06* (2013.01); *C12R 1/865* (2013.01); *C12G 2200/05* (2013.01); *C12Y 101/01001* (2013.01); *C12Y 401/01001* (2013.01)

(58) Field of Classification Search
None
See application file for complete search history.

(56) References Cited

U.S. PATENT DOCUMENTS

2011/0306083 A1* 12/2011 Mucha ..................... C12N 1/00
435/29

OTHER PUBLICATIONS

Kurylenko ("Metabolic engineering and classical selection of the methyltrophic thermotolerant yeast *Hansenula polymorpha* for improvement of high temperature xylose alcoholic fermentation" Microbial Cell Factories, Aug. 2014). (Year: 2014).*

* cited by examiner

*Primary Examiner* — Robert J Yamasaki
*Assistant Examiner* — Charles Zoltan Constantine
(74) *Attorney, Agent, or Firm* — Andrew F. Nilles

(57) ABSTRACT

Described herein are new approaches for the selection of *S. cerevisiae* strains with increased ethanol production from hydrolyzed starch derived sugars. An industrial production strain of *Saccharomyces cerevisiae* AS400 was subjected to positive selection of mutants resistant to toxic concentrations of oxythiamine, trehalose, 3-bromopyruvate, glyoxylic acid, and glucosamine. The selected mutants are characterized by 5-8% increase in ethanol yield (g g$^{-1}$ of consumed glucose) as compared to the parental industrial ethanol-producing strain. A multiple-step selection approach that consisted of the sequential selection using glyoxylic acid, glucosamine and bromopyruvate as selective agents resulted in a 12% increase in ethanol yield during fermentation on industrial media. These results indicate that the selection methods provided herein are useful for producing a variety of strains that are promising candidates for industrial ethanol production.

13 Claims, 4 Drawing Sheets

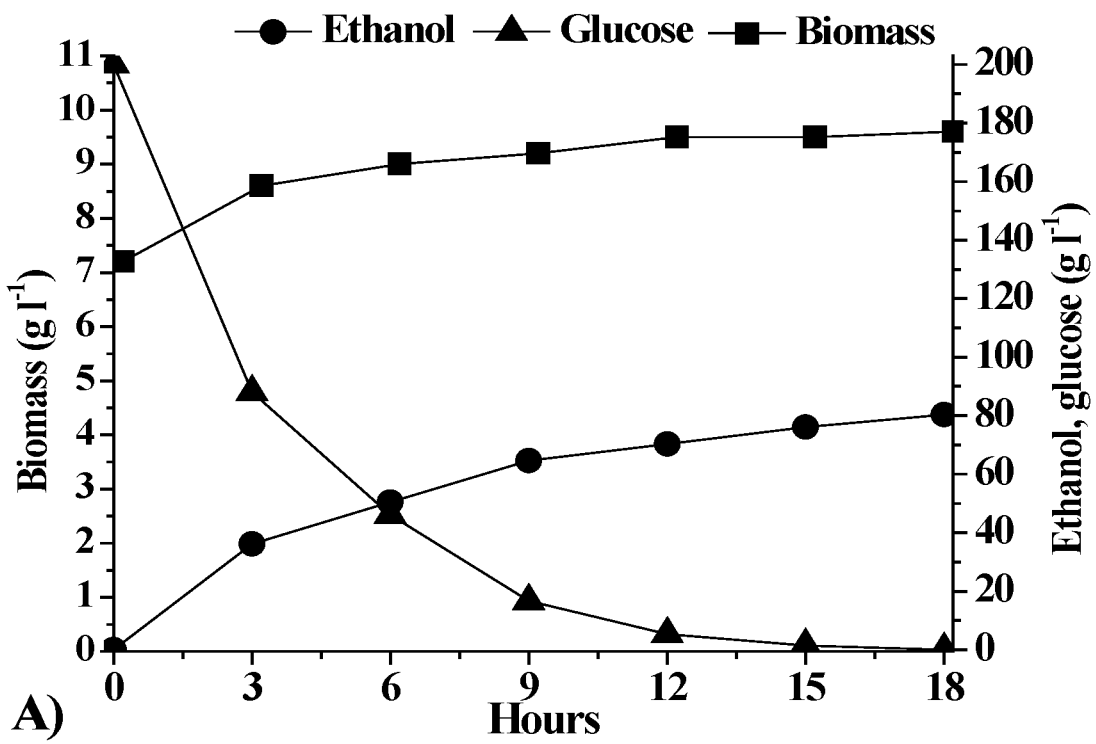
FIG. 1: AS400 fermentation
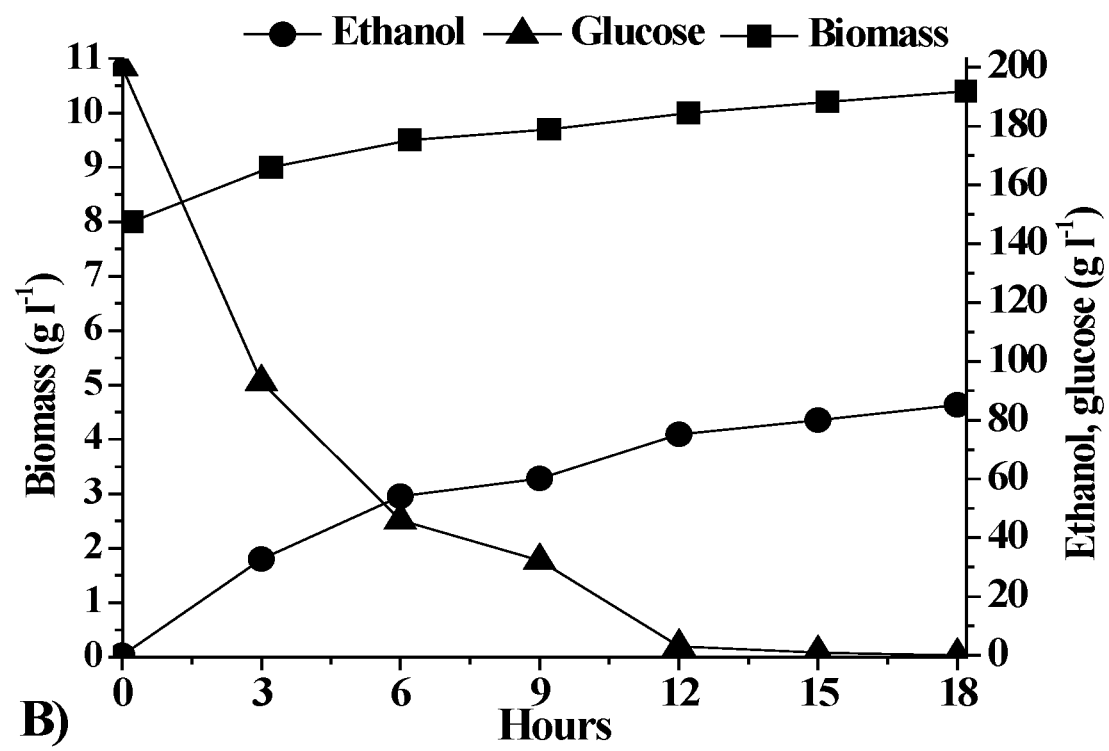
FIG. 2: AS400-567 fermentation

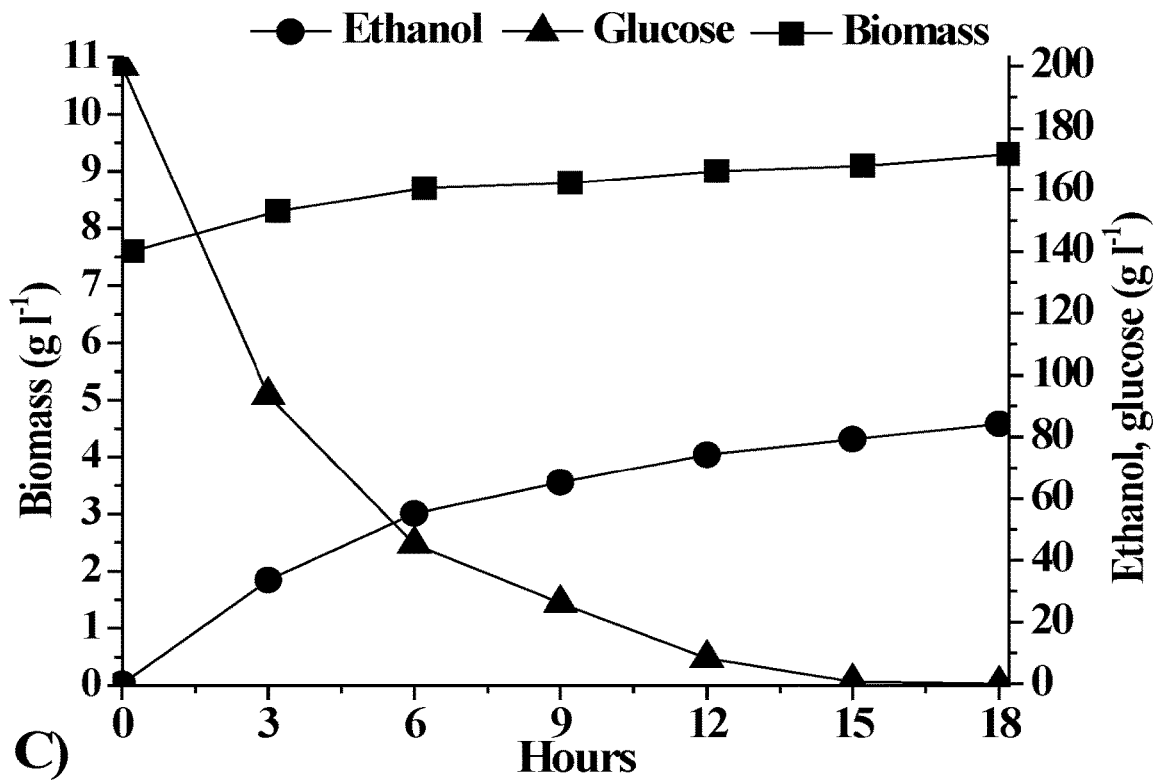
FIG. 3: AS400-543 fermentation
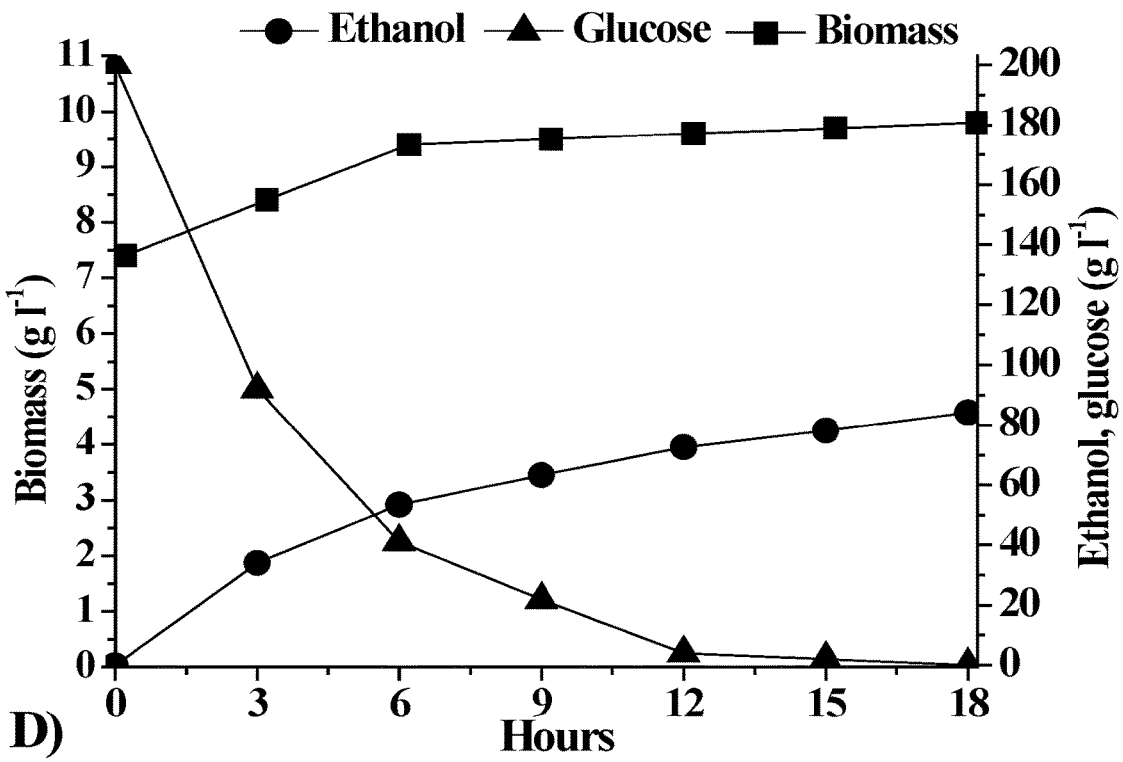
FIG. 4: AS400-617 fermentation

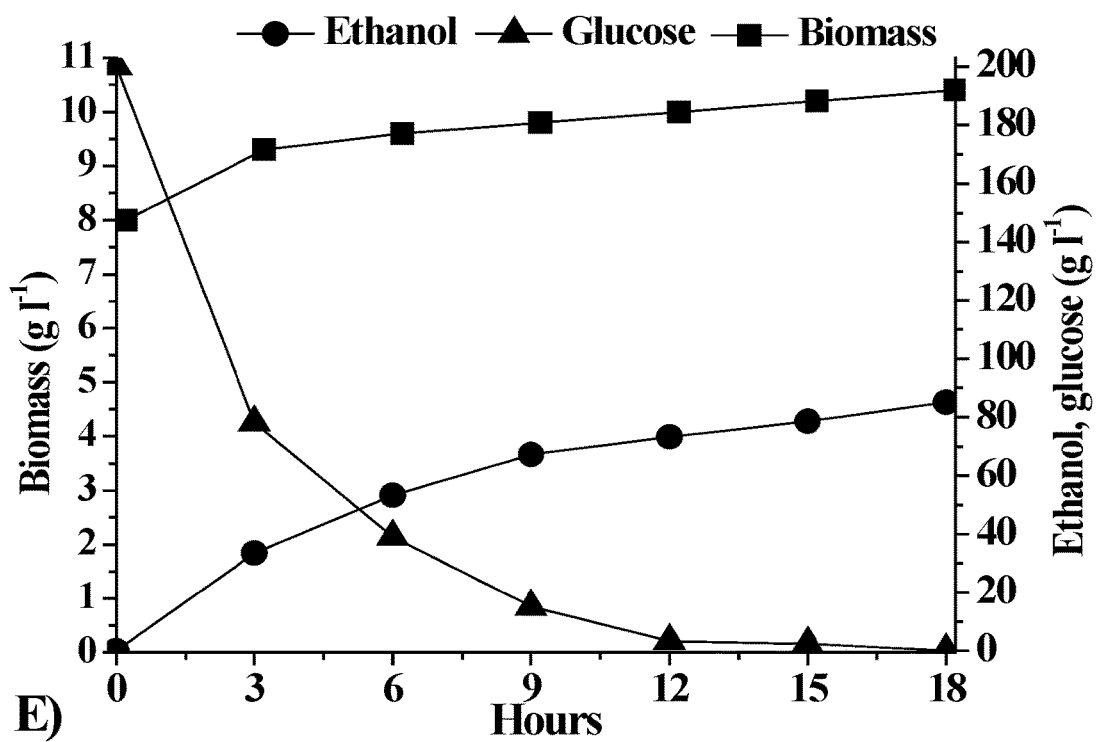
FIG. 5: AS400-510 fermentation
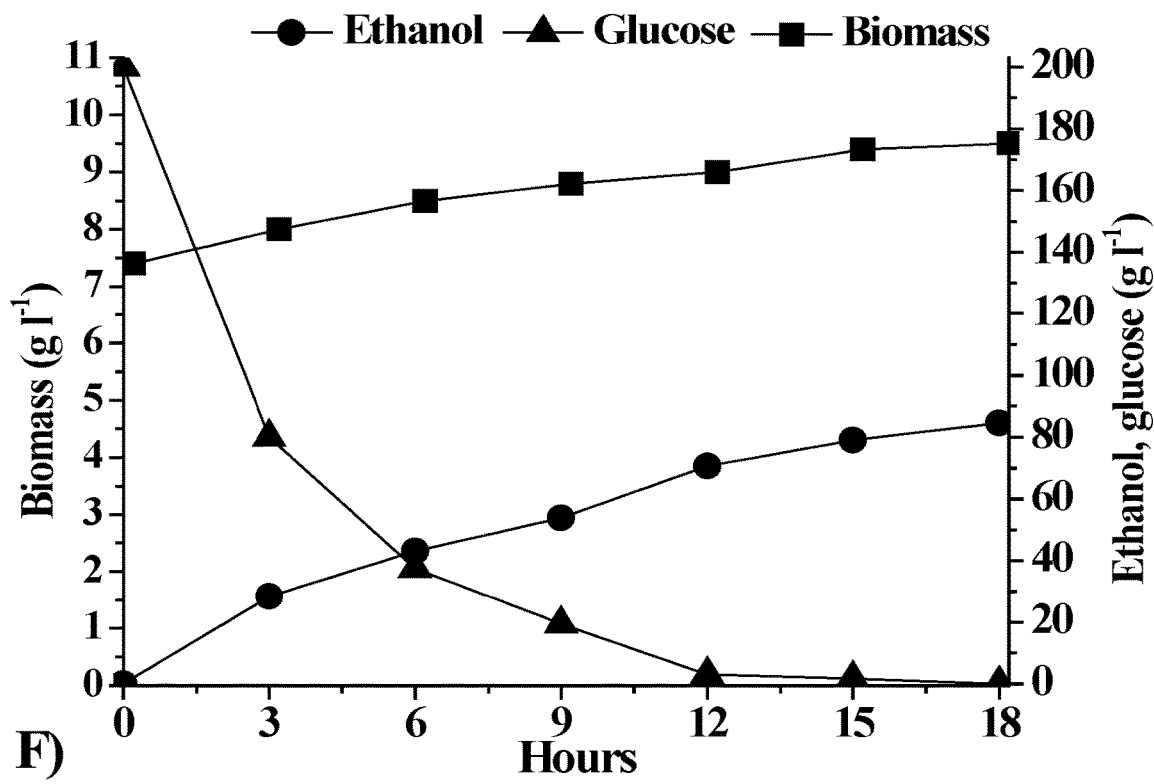
FIG. 6: AS400-128 fermentation

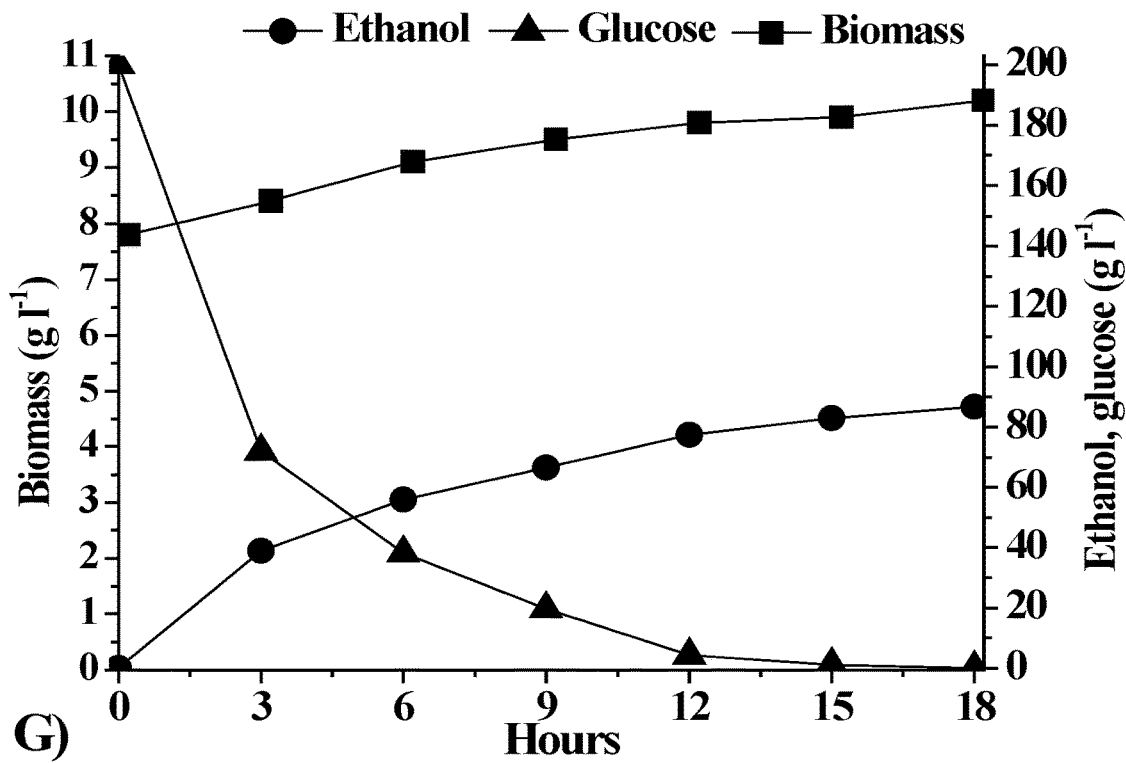
FIG. 7: AS400-510-42 fermentation
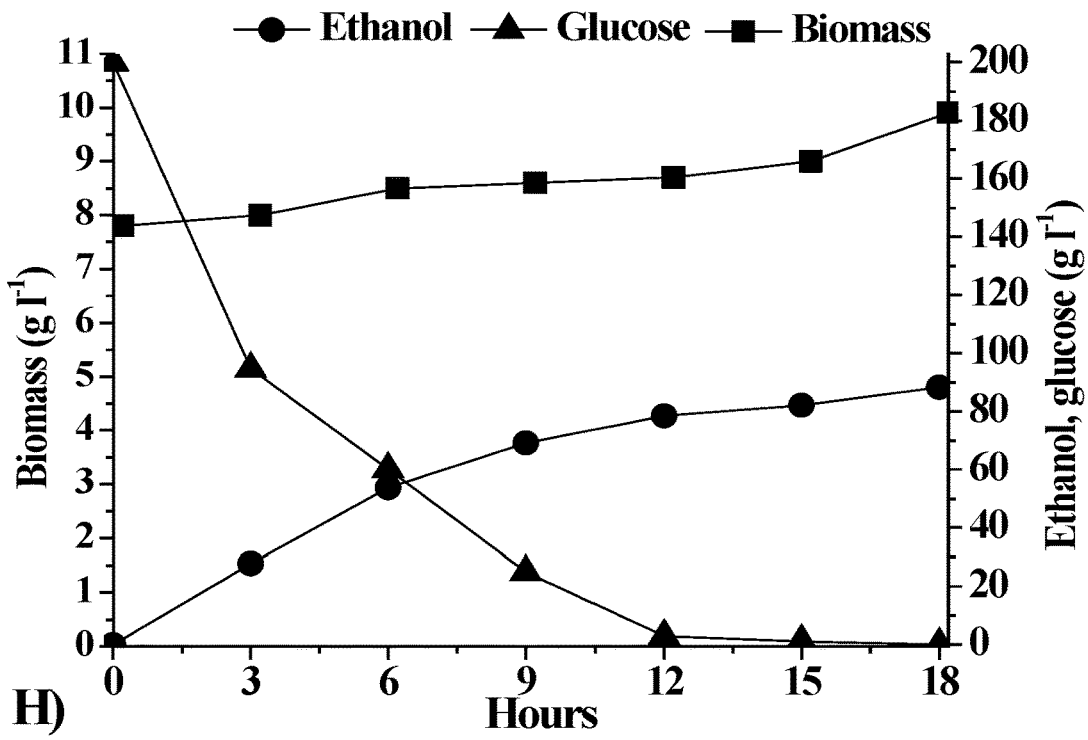
FIG. 8: AS400-510-42-214 fermentation

METHODS FOR THE POSITIVE SELECTION OF ETHANOL OVERPRODUCING MUTANTS FROM *SACCHAROMYCES CEREVISIAE*

CROSS REFERENCE TO RELATED APPLICATION[S]

This application claims priority to U.S. provisional application No. 62/145,606 entitled "NEW METHODS FOR THE POSITIVE SELECTION OF ETHANOL OVERPRODUCING MUTANTS FROM *SACCHAROMYCES CEREVISIAE*" filed Apr. 10, 2015 which is incorporated herein by reference in its entirety.

BACKGROUND OF THE INVENTION

Today the biofuel industry primarily produces ethanol from traditional feedstocks such as cereal crops like corn and wheat and sugar crops like sugar cane and sweet sugar beet.

The fermentation of plant carbohydrates by yeast dates back to the Neolithic period [1]. Today, yeasts are widely used in many biotechnological processes, with the largest use for the production of alcoholic beverages such as beer and wine and fuel ethanol. The yeast *Saccharomyces cerevisiae* is the predominant microorganism for industrial ethanol production. This yeast is characterized by several desirable industrial properties which include fast growth, efficient glucose anaerobic metabolism, high ethanol productivity and yield, and tolerance to several environmental stress-factors, such as high ethanol concentration and low oxygen level [2]. In spite of good ethanol yields from glucose and sucrose, the yield from these sugars can be further increased. There are several approaches that can be employed for this, which include genetic engineering techniques that target the redirection of yeast metabolism towards increased yield of ethanol production from carbohydrates by reducing co-product generation [3]. Particularly, this can be achieved through the reduction of glycerol and biomass synthesis, since these represent the major by-products made during a bioethanol production. During anaerobic growth of *S. cerevisiae*, glycerol serves as an essential electron sink for re-oxidizing reduced NADH generated during biosynthesis of ethanol. The employment of engineering approaches, which aim to change cellular redox metabolism via reduced formation of cytosolic NADH, resulted in the reduction of glycerol production with increase in ethanol yield [4, 5, 6, 7]. Decreasing biomass accumulation is an alternative way to increase ethanol yield from sugar consumed. The extent of biomass accumulation is dependent on the availability of energy in the form of ATP. If cellular ATP yield is decreased, it was anticipated that an increase in ethanol yield will result [8]. As predicted, increase in ethanol production was demonstrated using metabolic engineering approaches via the introduction of ATP-hydrolyzing futile cycles in yeast through the deregulation of some of the gluconeogenic enzymes [9]. A positive effect on ethanol production was also accomplished by the overexpression of ATPase [10] or the alkaline phosphatase Pho8 which can also hydrolyze ATP [11].

Though redirecting yeast metabolism towards increasing ethanol production using genetic engineering approaches is relatively easy to achieve, the usage of genetically modified strains for ethanol production, mainly in wine yeast, is not accepted in many parts of the world due to consumer's resistance to the use of genetically modified organisms (GMO) for beverage alcohol [12]. For this reason, the use of non-GMO approaches, which consist of traditional selection and adaptive evolution, must be relied on developing new improved strains [13]. Traditional selection and adaptive evolution involve applying culture conditions that provide a selection pressure favoring the growth of mutants within a population that confer the trait of interest. Thus, the culturing of cell populations in a specific selective environment will direct the accumulation of adaptation towards a desired phenotype [13, 14, 15]. There are several excellent examples that illustrate the usefulness of this approach to the selection of anaerobical xylose utilizing yeast strains [16], yeast with enhanced maltose utilization and osmotolerance [17], yeast with enhanced ethanol tolerance [18] and yeast with improved fermentation rate with decreased formation of acetate [19].

In the present disclosure, there is described new methods for positive selection of *S. cerevisiae* strains with enhanced ethanol production phenotypes. The methods are exemplified using industrial *S. cerevisiae* AS400 strain that is used for bioethanol production at Archer Daniels Midland Company (Decatur, Ill., USA). The selective agents oxythiamine, trehalose, 3-bromopyruvate, glyoxylic acid and glucosamine, were used in this description and chosen for their inhibitory effect on the enzymes involved in alcoholic fermentation and stress response.

SUMMARY OF THE INVENTION

The present disclosure describes a method of making a *S. cerevisiae* strain with enhanced ethanol producing characteristics comprising, contacting a culture of a parent strain of *S. cerevisiae* with a sufficient amount of a first selection agent selected from the group consisting of oxythiamine, trehalose, bromopyruvate, glyoxylic acid and glucosamine for the selection agent to be toxic to the parent strain; growing the contacted culture on a plating medium containing a sugar as a carbon source; selecting candidate spontaneous mutant strains of the culture that grow on the plating medium, and measuring an ethanol producing characteristic of the candidate spontaneous mutant strains to determine whether the candidate strain demonstrates enhanced ethanol production characteristics in comparison to the parent strain and if so, obtaining the *S. cerevisiae* strain with enhanced ethanol producing characteristics.

Certain embodiments include a method wherein the obtained spontaneous mutant strain with enhanced ethanol production characteristics is contacted with an amount of a second selection agent selected from the group consisting of oxythiamine, trehalose, bromopyruvate, glycoxylic acid and glucosamine for the selection agent to be toxic to the strain, wherein the second selection agent differs from the first selection agent; and repeating the growing, selecting and measuring acts to obtain a second spontaneous mutant strain having enhanced ethanol production characteristics in comparison to the first obtained spontanerous mutant strain.

Further embodiments include a method wherein the enhanced ethanol producing characteristic is at least one of: increased ethanol production measured as wt ethanol produced per volume, increased ethanol productivity measured as wt ethanol produced per volume per unit time, increased ethanol yield defined by wt ethanol produced per wt sugar fed to the strain, and increased specific ethanol productivity defined by wt ethanol produced per weight *S. cerevisiae* biomass per unit time.

Another aspect of the present disclosure includes a *S. cerevisiae* strain with enhanced ethanol producing characteristics made by any of the methods as described this far.

Certain embodiments include a *S. cerevisiae* strain that is an industrial ethanol production strain. Specific exemplary embodiments include a *S. cerevisiae* strain selected from the group consisting of AS400-567, AS400-543, AS400-617, AS400-510, AS400-128, AS400-510-42, and AS400-42-214. Other embodiments include a *S. cerevisiae* strain derived from a parent selected from the group consisting of AS400-567, AS400-543, AS400-617, AS400-510, AS400-128, AS400-510-42, and AS400-42-214.

Additional aspects of the invention include a method of producing ethanol comprising fermenting a sugar with a *S. cerevisiae* strain selected from the group consisting of AS400-567, AS400-543, AS400-617, AS400-510, AS400-128, AS400-510-42, and AS400-42-214 or a strain derived from such. Further embodiments include a method of separating the ethanol produced by the fermentation of a strain selected from the group consisting of AS400-567, AS400-543, AS400-617, AS400-510, AS400-128, AS400-510-42, and AS400-42-214 or a strain derived from such.

Another aspects of the present invention includes a method of making a *S. cerevisiae* strain with enhanced ethanol producing characteristics comprising, contacting a culture of a parent strain of *S. cerevisiae* with a sufficient amount of a first selection agent selected from the group consisting of oxythiamine, trehalose, glycoxylic acid and glucosamine for the selection agent to be toxic to the parent strain; growing the contacted culture on a plating medium containing a sugar as a carbon source; selecting candidate spontaneous mutant strains of the culture that grow on the plating medium, and measuring an ethanol producing characteristic of the candidate spontaneous mutant strains to determine whether the candidate strain demonstrates enhanced ethanol production characteristics in comparison to the parent strain and if so, obtaining the *S. cerevisiae* strain with enhanced ethanol producing characteristics.

An additional aspect of the invention includes a method wherein the obtained spontaneous mutant strain with enhanced ethanol production characteristics that has been contacted with a first selection agent selected from the group consisting of oxythiamine, trehalose, glycoxylic acid and glucosamine is further contacted with an amount of a second selection agent selected from the group consisting of oxythiamine, trehalose, glycoxylic acid and glucosamine for the selection agent to be toxic to the strain, wherein the second selection agent differs from the first selection agent; and repeating the growing, selecting and measuring acts to obtain a second spontaneous mutant strain having enhanced ethanol production characteristics in comparison to the first obtained spontanerous mutant strain.

BRIEF DESCRIPTION OF THE DRAWINGS

All of the figures depict growth, glucose consumption and ethanol production during alcoholic fermentation of mutants and initial AS400 strains. Several strains were cultured under semi anaerobic conditions in YNB medium with 200 g l$^{-1}$ D-glucose and were incubated at 34° C., shaking at 120 rpm using. The squares, triangles and circles of each figure correspond to biomass accumulation (g of biomass l$^{-1}$ of medium), glucose consumption (g of glucose l$^{-1}$ of medium) and ethanol production (g of ethanol l$^{-1}$ of medium), respectively. Additional information can be found in Table 1 about each of these fermentations.

FIG. 1 depicts a fermentation as described above using the strain AS400.

FIG. 2 depicts a fermentation as described above using the strain AS400-567.

FIG. 3 depicts a fermentation as described above using the strain AS400-543.

FIG. 4 depicts a fermentation as described above using the strain AS400-617.

FIG. 5 depicts a fermentation as described above using the strain AS400-510.

FIG. 6 depicts a fermentation as described above using the strain AS400-128.

FIG. 7 depicts a fermentation as described above using the strain AS400-510-42.

FIG. 8 depicts a fermentation as described above using the strain AS400-510-42-214.

DETAILED DESCRIPTION OF THE INVENTION

The *S. cerevisiae* strain AS400 (Archer Daniels Midland Company (Decatur, Ill., USA)) was used as the parental strain for the selection of improved strains. All chemicals used through the work were obtained from Sigma, USA, unless otherwise noted.

*S. cerevisiae* strains were routinely cultured at 30° C. Yeast strains were maintained in rich YPD (1% yeast extract, 1% peptone and 2% glucose) or mineral YNB (0.67%, yeast nitrogen base without amino acids, (Difco, USA), 0.5% ammonium sulfate, 2% glucose) media. *S. cerevisiae* cells were grown overnight in YPD and washed twice with $H_2O$. For selection of ethanol overproducing mutants, a cell suspension of AS400 ($10^6$, $1.7 \times 10^6$ and $3.3 \times 10^6$ cells per plate d=90 mm) was plated on YNB solid medium with glucose (2%) as the carbon source supplemented with toxic concentrations of the selective agents, oxythiamine (118 mM), trehalose (1.31 M), 3-bromopyruvate (2.75 mM), glyoxylic acid (4 mM) or glucosamine (2.75 mM) and incubated for 7-14 days depending on selective agents. The minimal toxic concentrations of inhibitors were defined as the amount of the agent in YNB-glucose solid medium that totally inhibited growth of AS400 strain after plating $3.3 \times 10^6$ cells per plate. Single yeast colonies resistant to the selective agents were picked up, re-streaked on fresh YNB plates containing corresponding concentrations of reagent and used in fermentation experiments. The selected mutants were stable, maintaining resistance to the selective agents. Selected strains were also found to be stable in respect of their ability to produce increased amount of ethanol after 6 months of storage at −80° C. No cross-resistance to the different selection agents used was found in the mutants.

Corn steep liquor (CSL) is a by-product of corn wet-milling that is obtained after initial soaking corn grain in water prior to milling. CSL has been used as an effective low-cost fermentation nutrient supplement in several different fermentations [20]. CSL was used to supplement hydrolyzed corn meal as routinely used in industrial alcoholic fermentation processes in distillery and fuel-ethanol plants.

The CSL medium was prepared by combining two solutions that were prepared as described. Solution 1 was prepared by adding 200 g of corn meal (Melvit, Poland) mixed with 800 ml of deionized water and pH adjusted to 6.0 using NaOH. The enzyme alpha-amylase (Liquizyme SC) was added at a rate of 0.1 units of per gram of meal, and the slurry was liquified by heating the mixture to 80° C. for 30 minutes. To prepare Solution 2, 63 ml of the CSL concentrate (provided by ADM Company) containing ~50% dry solids was mixed with 137 ml of deionized water. The composition of CSL was described elsewhere [21]. Prior to use, the two solutions were autoclaved, cooled, and then combined and mixed. The enzyme glucoamylase (Liquizyme SC) was added in the amount of 0.2 units of glucoamylase per gram of meal to sterile flasks, and the flasks were incubated at 28° C. Glucose concentration was measured in the control flasks without yeast inoculation at 200 g $l^{-1}$ in the CSL medium prepared.

For ethanol fermentation, all strains were tested using YNB medium that was supplemented with 20% glucose or by using a medium containing corn CSL supplemented with hydrolyzed corn meal as the primary carbon source.

For alcoholic fermentation, cells of AS400 strain and its derivatives were grown overnight in 100 ml of YPD medium in 300 ml Erlenmeyer flasks and then used to inoculate 20 ml aliquots of mineral YNB medium supplemented with 200 g $l^{-1}$ glucose or CSL medium supplemented with hydrolyzed meal in 50 ml Erlenmeyer flasks. An initial biomass concentration of 8 g (dry weight) $l^{-1}$ was used for fermentation in YNB medium. For CSL medium, an initial biomass concentration of 10 g (dry weight) $l^{-1}$ was used (this is the cell density normally used in industrial ethanol fermentation) [22]. Fermentation was carried out at a temperature of 34° C. with limited aeration using a gyratory shaker at a setting of 120 rev. $min^{-1}$. Samples were taken every 3 hours for YNB medium or 12 hours for CSL medium. Fermentation experiments were performed in at least triplicate to ensure reproducibility.

The concentration of ethanol in fermentation media was determined using alcohol oxidase/peroxidase-based enzymatic kit "Alcotest" [23, 24]. The biomass was determined using turbidity with a Helios Gamma spectrophotometer (OD, 600 nm; cuvette, 10 mm) with gravimetric calibration. Glucose concentration was determined using the "Diagluc" assay kit (UBT, Lviv) [23]. All samples were assayed in duplicate.

Oxythiamine is a thiamine antagonist that, after conversion to oxythiamine pyrophosphate, binds to the active centers of thiamine-dependent enzymes. It was shown that *S. cerevisiae* cells treated by oxythiamine possessed higher specific activity of transketolase and pyruvate decarboxylase after 12 h of cultivation [25]. Transketolase is a crucial enzyme of the pentose phosphate pathway, providing metabolic intermediate (glyceraldehyde-3-phosphate and fructose-6-phosphate) for glycolysis and the substrates (NADPH, ribose-phosphate) for macromolecule synthesis. Pyruvate decarboxylase in turn is the key enzyme directing carbon flux from pyruvate to ethanol. The present inventors speculated that yeast strains resistant to oxythiamine would possess increased pyruvate to acetaldehyde conversion that would result in increased production of ethanol. Several strains, derivatives of AS400, were therefore selected on the selective media supplemented with toxic concentration of oxythiamine (118 mM). Among these strains, AS400-567 was demonstrated to in fact have an increase in ethanol synthesis during fermentation on YNB medium. This strain accumulated 6% more ethanol relative to the parental strain AS400 during fermentation producing 85.2 g $l^{-1}$ of ethanol versus 80.3 g $l^{-1}$ for AS400 (Table 1, FIG. 1. And FIG. 2). Due to similar biomass accumulation and complete glucose consumption during fermentation, ethanol productivity (4.73 g $l^{-1}$ $h^{-1}$), specific ethanol productivity (1.97 g $g^{-1}$ biomass $h^{-1}$) and ethanol yield (0.426 g of ethanol $g^{-1}$ of consumed glucose) for strain AS400-567 were also increased for 6% as compared to AS400. Alcoholic fermentation in CSL medium demonstrated a 7% increase in ethanol production for strain AS400-567 for a total ethanol production of 90.5 g $l^{-1}$, as compared to strain AS400 which produced 84.6 g $l^{-1}$ of ethanol (Table 1). Ethanol yield for strain AS400-567 was also increased on 7% since this and parental strains consumed glucose completely (Table 1). Measurement of the productivity of ethanol synthesis per biomass for this and other strains was not carried out in CSL medium as it contains many insoluble particles that interfered with cell biomass measurement using direct dry weight or by optical density analyses.

During alcoholic fermentation, yeast cells are subjected to stress that could affect their viability and fermentation efficiency. Trehalose functions as one of the major stress protectants and the synthesis of trehalose is induced by several documented stress conditions at the transcriptional level in *S. cerevisiae* [26]. Trehalose-6-phosphate synthase is the key enzyme involved in trehalose synthesis and is known to be inhibited by high concentrations of trehalose [27]. Yeast mutants resistant to increased concentrations of trehalose may have elevated intracellular concentration of this disaccharide with subsequent beneficial effect of trehalose on ethanol production. Strain AS400 was subjected to a selection on the medium containing toxic concentration of trehalose (1.31 M). Several trehalose resistant strains were selected after 14 days of incubation. The trehalose resistant strain AS400-543 had a 5% increase in ethanol production (84.3 g $l^{-1}$), ethanol productivity (4.68 g $l^{-1}$ $h^{-1}$) and an ethanol yield (0.422 g $g^{-1}$ of consumed glucose) as compared to the parental strain during fermentation on YNB medium (Table 1, FIG. 3). However, specific ethanol productivity of this strain was increased by 48%, reaching 2.75 g $g^{-1}$ biomass $h^{-1}$ as calculated from a 1.6 fold decrease in specific growth rate (Table 1, FIG. 3). A similar increase in ethanol production and ethanol yield was observed for this trehalose resistant strain during fermentation on industrial CSL medium. Strain AS400-543 synthesized a total of 88.8 g $l^{-1}$ of ethanol, whereas strain AS400 produced a total of 84.6 g $l^{-1}$ of ethanol (Table 1). Ethanol yield reached 0.444 g $g^{-1}$ of consumed glucose providing 5% increase as compared to the parental strain (Table 1).

The present inventors speculated that yeast mutants resistant to bromopyruvate may have an increase in glycolysis with elevated amount of synthesized ethanol. The strain AS400-617 was selected on a medium supplemented with toxic concentration of this selective agent (2.75 mM). The bromopyruvate resistant strain was characterized by having up to 5% increase of ethanol production (84.1 g $l^{-1}$), a productivity (1.95 g $g^{-1}$ biomass $h^{-1}$) and an ethanol yield (0.421 g of ethanol $g^{-1}$ of consumed glucose) during fermentation on YNB medium when compared to the strain AS400 (Table 1, FIG. 4). Strain AS400-617 synthesized a total of 89.7 g $l^{-1}$ ethanol with up to 6% increase in ethanol accumulation when compared to initial strain AS400 in CSL medium (Table 1). Ethanol yield was also increased by 6% reaching 0.421 g $g^{-1}$ of the consumed glucose (Table 1).

Glyoxylic acid is a known irreversible inhibitor of pyruvate decarboxylase activity [31], the key enzyme in ethanol synthesis. Therefore, selection of ethanol overproducers was carried out using a YNB medium containing 4 mM glyoxylic acid. Several resistant colonies were obtained from AS400 after 5-8 days of plate incubation and subjected to testing for ethanol production from glucose. The isolated strain AS400-510 had a 6% elevation of total ethanol production (85.1 g $l^{-1}$), a productivity (1.97 g $g^{-1}$ biomass $h^{-1}$) and an increase in ethanol yield (0.426 g $g^{-1}$ of consumed glucose) during alcoholic fermentation in YNB medium (Table 1, FIG. 5). During fermentation on CSL medium, a total of 91.4 g $l^{-1}$ of ethanol was produced with an ethanol yield (0.457 g $g^{-1}$ of consumed glucose) for an 8% increase in ethanol production and yield over AS400 (Table 1).

Glucosamine (2-deoxy-2-aminoglucose) is a structural analog of glucose. Due to the absence of hydroxyl at the second position, this compound cannot be isomerized to the ketohexose (analog of fructose) by the glycolytic enzyme phosphoglucoisomerase [32]. This leads to disruption of the glycolysis at this step. The glucosamine resistant mutants can be defective in glucose uptake, but this is very unlikely during the selection on glucose as the sole carbon source. Other explanation for this could be the depression of PGI1 only or the entire regulon involved in regulation of the majority of glycolytic enzymes. The present inventors speculated that this last event would result in an increase of glucose flux through glycolysis pathway. Glucosamine was therefore used as selective agents for positive selection of S. cerevisiae ethanol overproducers. Toxic concentrations of this selective agent was found to be 2 mM. Strains AS400 and its derivative AS400-510 isolated as a glyoxylic acid resistant mutant were subjected for selection on a medium containing glucosamine. The selection on the YNB medium containing 2 mM of glucosamine resulted in the isolation of several resistant mutants after 14 days of incubation. The selected mutants were tested for ethanol production from glucose. The glucosamine resistant mutant derived from the AS400 (strain AS400-128) had an 5% increase in ethanol production (84.6 g $l^{-1}$), higher ethanol productivity (4.7 g $l^{-1}$ $h^{-1}$) and an increase in ethanol yield (0.423 g $g^{-1}$ of consumed glucose), while the specific ethanol productivity (2.24 g $g^{-1}$ biomass $h^{-1}$) was increased by 20% due to reduction of its specific growth rate (0.117 g $l^{-1}$ $h^{-1}$) by 12%, as compared to the parental strain, during fermentation on YNB medium (Table 1, FIG. 6). The highest ethanol titer for strain AS400-128 during CSL fermentation was 89.6 g $l^{-1}$, whereas the initial strain synthesized 84.6 g $l^{-1}$ of ethanol, providing 6% increase of ethanol production and ethanol yield (Table 1). The strain AS400-510-42, that was derived from AS400-510, had an 8% increase in ethanol production (86.7 g $l^{-1}$), a specific ethanol productivity (2.01 g $g^{-1}$ biomass $h^{-1}$) and ethanol yield (0.434 g $g^{-1}$ of consumed glucose) as compared to the AS400 during fermentation on YNB medium (Table 1, FIG. 7). Strain AS400-510-42 synthesized 93.0 g $l^{-1}$ of ethanol, while the initial strain AS400 produced only 84.6 g $l^{-1}$ of ethanol during fermentation on CSL medium (Table 1). Thus, the increase of ethanol production and ethanol yield for this strain reached 10%.

It was further speculated that mutants obtained by sequential selection for resistance to two of the present selection agents may further increases in ethanol production characteristics. A double cross selection for glycoxylic acid and glucosamine resistance showed an increase of the ethanol production. This strain was labeled AS400-510-42. These results encouraged inventors to perform an additional round of the selection. Strain AS400-510-42 was used for the selection of bromopyruvate resistant derivatives. Several mutants were selected on the medium supplemented with 2.75 mM of bromopyruvate. Among them, strain AS400-510-42-214 which had a 10% increase in ethanol production (88.3 g $l^{-1}$), an ethanol productivity (4.91 g $l^{-1}$ $h^{-1}$) and an ethanol yield (0.442 g $g^{-1}$ of consumed glucose), while the specific ethanol productivity (2.34 g $g^{-1}$ biomass $h^{-1}$) was increased by 26% as a result of reduction of the specific growth rate (0.117 g $l^{-1}$ $h^{-1}$) on 12%, during fermentation on YNB medium (Table 1, FIG. 8). Strain AS400-510-42-214 had the highest amount of synthetized ethanol among all isolated mutants reaching a total of 94.8 g $l^{-1}$ of ethanol production on CSL medium. Strain AS400-510-42-214 showed a 12% increase in ethanol production and ethanol yield when compared to the parental strain AS400 (Table 1).

Applying the new simple positive methods for selection of S. cerevisiae strains with increased ethanol production on industrial medium supplemented with hydrolyzed corn meal, the inventors were able to demonstrate an increase in ethanol synthesis from 5 to 8% when compared to the parental industrial strain. The 5% increase in ethanol synthesis and ethanol yield was reached for strain selected on toxic concentration of trehalose, while mutants selected on bromopyruvate or glucosamine, oxythiamine and glyoxylic acid possessed 6%, 7% and 8% increase in ethanol production and yield, respectively. The combination of glyoxylic acid and glucosamine or glyoxylic acid, glucosamine and bromopyruvate for two- or three-steps selection schemes led to 10 or 12% increase of ethanol production and yield as compared to the parental strain. Strains selected on trehalose, glucosamine or glyoxylic acid, glucosamine and bromopyruvate for one- or three-step selections showed an increase in specific ethanol productivity, which is a result of the decrease in biomass accumulation during fermentation procedure. Selected strains described in this work possessed very similar kinetics for glucose consumption. While not being bond by theory, it is possible that the observed increase in ethanol accumulation is caused by a decrease in accumulation of fermentation by-products, e.g. biomass, glycerol or acetate. The identification of the mutated genes in the selected mutants is the subject of our subsequent work.

For each type of mutants, more than 30 selected strains were selected and evaluated for the ethanol production from glucose. From 55 to 65% of isolated mutants resistant to the applied selective agents showed an increase in ethanol synthesis. On average, the ethanol yield in the analyzed strains was increased by 5-6% as compared to the parental strain. Relatively high percentage of ethanol overproducers lead us to conclude that our approaches represent new methods for positive selection of ethanol overproducers.

TABLE 1

Growth rate, ethanol production, productivity, specific productivity and yield of S. cerevisiae mutants resistant to oxythiamine, trehalose, bromopyruvate, glyoxylic acid, glucosamine and initial strain AS400 during alcoholic fermentation of on YNB medium supplemented with 20% glucose and CSL medium with hydrolyzed meal indicated in brackets.

| Strain | Selective agent | Specific growth rate g $l^{-1}h^{-1}$ | Ethanol g $l^{-1}$ | Ethanol productivity g $l^{-1}h^{-1}$ | Specific ethanol productivity g $g^{-1}$ biomass $h^{-1}$ | Ethanol yield g $g^{-1}$ of consumed glucose |
|---|---|---|---|---|---|---|
| AS400 | — | 0.133 ± 0.003 | 80.3 ± 1.5 (84.6 ± 1.0) | 4.46 ± 0.08 (3.53 ± 0.03) | 1.86 ± 0.03 | 0.402 ± 0.007 (0.423 ± 0.005) |

TABLE 1-continued

Growth rate, ethanol production, productivity, specific productivity and yield of *S. cerevisiae* mutants resistant to oxythiamine, trehalose, bromopyruvate, glyoxylic acid, glucosamine and initial strain AS400 during alcoholic fermentation of on YNB medium supplemented with 20% glucose and CSL medium with hydrolyzed meal indicated in brackets.

| Strain | Selective agent | Specific growth rate g $l^{-1}h^{-1}$ | Ethanol g $l^{-1}$ | Ethanol productivity g $l^{-1}h^{-1}$ | Specific ethanol productivity g $g^{-1}$ biomass $h^{-1}$ | Ethanol yield g $g^{-1}$ of consumed glucose |
|---|---|---|---|---|---|---|
| AS400-567 | oxythiamine | 0.133 ± 0.004 | 85.2 ± 1.6 (90.5 ± 0.9) | 4.73 ± 0.09 (3.77 ± 0.04) | 1.97 ± 0.04 | 0.426 ± 0.008 (0.453 ± 0.004) |
| AS400-543 | trehalose | 0.083 ± 0.002 | 84.3 ± 1.6 (88.8 ± 0.9) | 4.68 ± 0.09 (3.70 ± 0.03) | 2.75 ± 0.06 | 0.422 ± 0.008 (0.444 ± 0.005) |
| AS400-617 | bromopyruvate | 0.133 ± 0.003 | 84.1 ± 1.5 (89.7 ± 1.0) | 4.67 ± 0.09 (3.74 ± 0.03) | 1.95 ± 0.03 | 0.421 ± 0.007 (0.449 ± 0.005) |
| AS400-510 | glyoxylic acid | 0.133 ± 0.004 | 85.1 ± 1.6 (91.4 ± 0.9) | 4.73 ± 0.09 (3.81 ± 0.03) | 1.97 ± 0.04 | 0.426 ± 0.007 (0.457 ± 0.005) |
| AS400-128 | glucosamine | 0.117 ± 0.003 | 84.6 ± 1.7 (89.6 ± 0.9) | 4.70 ± 0.09 (3.73 ± 0.04) | 2.24 ± 0.04 | 0.423 ± 0.008 (0.448 ± 0.005) |
| AS400-510-42 | glyoxylic acid, glucosamine | 0.133 ± 0.004 | 86.7 ± 1.7 (93.0 ± 0.9) | 4.82 ± 0.09 (3.88 ± 0.03) | 2.01 ± 0.04 | 0.434 ± 0.008 (0.465 ± 0.004) |
| AS400-510-42-214 | glyoxylic acid, glucosamine, bromopyruvate | 0.117 ± 0.003 | 88.4 ± 1.5 (94.8 ± 1.0) | 4.91 ± 0.08 (3.95 ± 0.04) | 2.34 ± 0.04 | 0.442 ± 0.008 (0.474 ± 0.005) |

(±) - absolute error

REFERENCES

[1] Dashko S., Zhou N., Compagno C., Piškur J., Why, when, and how did yeast evolve alcoholic fermentation?, FEMS Yeast Res., 2004, 14(6), 826-832.

[2] Piškur J., Langkjaer R. B., Yeast genome sequencing: the power of comparative genomics, Mol. Microbiol., 2004, 53, 381-389.

[3] Gombert A. K., van Maris A. J., Improving conversion yield of fermentable sugars into fuel ethanol in 1st generation yeast-based production processes, Curr. Opin. Biotechnol., 2015, 7, 33C, 81-86.

[4] Nissen T. L., Kielland-Brandt M. C., Nielsen J., Villadsen J., Optimization of ethanol production in *Saccharomyces cerevisiae* by metabolic engineering of the ammonium assimilation, Metab. Eng., 2000, 2, 69-77.

[5] Bro C., Regenberg B., Forster J., Nielsen J., In silico aided metabolic engineering of *Saccharomyces cerevisiae* for improved bioethanol production, Metab. Eng. 2006, 8, 102-111.

[6] Guo Z., Zhang L., Ding Z., Shi G., Minimization of glycerol synthesis in industrial ethanol yeast without influencing its fermentation performance, Metab. Eng., 2011, 13, 49-59.

[7] Zhang L., Tang Y., Guo Z., Ding Z., Shi G., Improving the ethanol yield by reducing glycerol formation using cofactor regulation in *Saccharomyces cerevisiae*, Biotechnol. Lett., 2011, 33, 1375-1380.

[8] de Kok S., Kozak B. U., Pronk J. T., Van Maris A., Energy coupling in *Saccharomyces cerevisiae*: selected opportunities formetabolic engineering, FEMS Yeast Res., 2012, 12, 387-397.

[9] Navas M. A., Cerdan S., Gancedo J. M., Futile cycles in *Saccharomyces cerevisiae* strains expressing the gluconeogenic enzymes during growth on glucose, Proc. Nat. Acad. Sci. USA, 1993, 90, 1290-1294.

[10] Dmytruk K. V., Semkiv M. V., Sibirny A. A., Ethanol yield and reduction of biomass accumulation in the recombinant strain of *Saccharomyces cerevisiae* overexpressing ATPase, WO/2010/151866. 2010.

[11] Semkiv M. V., Dmytruk K. V., Abbas C. A., Sibirny A. A., Increased ethanol accumulation from glucose via reduction of ATP level in a recombinant strain of *Saccharomyces cerevisiae* overexpressing alkaline phosphatase, BMC Biotechnol., 2014, 14, 42.

[12] Grossmann M., Kiessling F., Singer J., Schoeman H., Schröder M. B., von Wallbrunn C., Genetically modified wine yeasts and risk assessment studies covering different steps within the wine making process, Ann. Microbiol., 2011, 61, 103-115.

[13] Chambers P. J., Bellon J. R., Schmidt S. A., Varela C., Pretorius I. S., Non-genetic engineering approaches to isolating and generating novel yeast for industrial applications, In: Kunze G., Satyanarayana T. (eds), Yeast biotechnology: Diversity and applications, Springer Science+Business Media, 433-457, 2009.

[14] Cakar Z. P., Seker U. O., Tamerler C., Sonderegger M., Sauer U., Evolutionary engineering of multiple-stress resistant *Saccharomyces cerevisiae*, FEMS Yeast Res., 2005, 5, 569-578.

[15] Zeyl C., The number of mutations selected during adaptation in a laboratory population of *Saccharomyces cerevisiae*, Genetics, 2005, 169, 1825-1831.

[16] Kuyper M., Toirkens M. J., Diderich J. A., Winkler A. A., van Dijken J. P., Pronk J. T., Evolutionary engineering of mixed-sugar utilization by a xylose-fermenting *Saccharomyces cerevisiae* strain, FEMS Yeast Res., 2005, 5, 925-934.

[17] Higgins V. J., Bell P. J. L., Dawes I. W., Attfield P. V., Generation of a novel *Saccharomyces cerevisiae* strain that exhibits strong maltose utilization and hyperosmotic resistance using nonrecombinant techniques, Appl. Environ. Microbiol., 2001, 67, 4346-4348.

[18] Stanley D., Fraser S., Chambers P. J., Rogers P., Stanley G. A., Generation and characterisation of stable ethanol-tolerant mutants of *Saccharomyces cerevisiae*, J. Ind. Microbiol. Biot., 2010, 37, 139-149.

[19] Cadiere A., Ortiz-Julien A., Camarasa C., Dequin S., Evolutionary engineered *Saccharomyces cerevisiae* wine yeast strains with increased in vivo flux through the pentose phosphate pathway, Metab. Eng., 2011, 13, 263-271.

[20] Lawford H. G., Rousseau J. D., Corn steep liquor as a cost-effective nutrition adjunct in high-performance *Zymomonas* ethanol fermentations, Applied Biochemistry and Biotechnology, Spring 1997, 63-65, 1, 287-304.
[21] Christianson D. D., Cavins J. F., Wall J. S., Steep liquor constituents, identification and determination of nonprotein nitrogenous substances in corn steep liquor., J. Agric. Food Chem., 1965, 13(3), 277-280.
[22] Lin Y., Tanaka S., Ethanol fermentation from biomass resources: current state and prospects, Appl. Microbiol. Biotechnol., 2006, 69, 627-642.
[23] Gonchar M. V., Sensitive method for quantitative determination of hydrogen peroxide and oxidase substrates in biological samples, Ukr. Biokhim. Zh., 1998, 70, 157-163.
[24] Gonchar M. V., Maidan M. M., Pavlishko H. M., Sibirny A. A., A new oxidase-peroxidase kit for ethanol assays in alcoholic beverages, Food. Technol. Biotechnol. 2001, 39, 37-42.
[25] Tylicki A., Czerniecki J., Dobrzyn P., Matanowska A., Olechno A., Strumilo S., Modification of thiamine pyrophosphate dependent enzyme activity by oxythiamine in *Saccharomyces cerevisiae* cells, Can. J. Microbiol., 2005, 51(10), 833-839.
[26] Kaino T., Takagi H., Gene expression profiles and intracellular contents of stress protectants in *Saccharomyces cerevisiae* under ethanol and sorbitol stresses, Appl. Microbiol. Biotechnol., 2008, 79, 273-283.
[27] Lippert K., Galinski E. A., Trueper H. G., Biosynthesis and function of trehalose in *Ectothiorhodospira halochloris*, Antonie Leeuwenhoek 1993, 63, 85-91.
[28] Ko Y. H., Pedersen P. L., Geschwind J. F., Glucose catabolism in the rabbit VX2 tumor model for liver cancer: characterization and targeting hexokinase, Cancer Lett., 2001, 173, 83-91.
[29] Geschwind J. F., Georgiades C. S., Ko Y. H., Pedersen P. L., Recently elucidated energy catabolism pathways provide opportunities for novel treatments in hepatocellular carcinoma, Expert Rev. Anticancer Ther., 2004, 4, 449-457.
[30] Kurylenko O. O., Ruchala J., Hryniv O. B., Abbas C. A, Dmytruk K. V., Sibirny A. A., Metabolic engineering and classical selection of the methylotrophic thermotolerant yeast *Hansenula polymorpha* for improvement of high-temperature xylose alcoholic fermentation, Microb. Cell. Fact., 2014, 13, 122.
[31] Uhlemann H., Schellenberger A., Glyoxylic acid as an active site marker of yeast pyruvate decarboxylase, FEBS Lett., 1976, 63, 37-39.
[32] Bekesi J. G., Molnar Z., Richard J., Winzler inhibitory effect of d-glucosamine and other sugar analogs on the viability and transplantability of ascites tumor cells, Cancer Res., 1969, 29, 353-359.

What is claimed is:

1. A method of making a *S. cerevisiae* strain with enhanced ethanol producing characteristics comprising,
    contacting a culture of a parent strain of *S. cerevisiae* with a sufficient amount of a first selection agent selected from the group consisting of oxythiamine, trehalose, bromopyruvate, glyoxylic acid and glucosamine for the selection agent to be toxic to the parent strain;
    growing the contacted culture on a plating medium containing a sugar as a carbon source;
    selecting candidate spontaneous mutant strains of the culture that grow on the plating medium;
    measuring an ethanol producing characteristic of the candidate spontaneous mutant strains to determine whether the candidate strain demonstrates enhanced ethanol production characteristics in comparison to the parent strain and if so, obtaining the *S. cerevisiae* strain with enhanced ethanol producing characteristics;
    contacting the obtained spontaneous mutant strain with enhanced ethanol production characteristics with an amount of a second selection agent selected from the group consisting of oxythiamine, trehalose, bromopyruvate, glyoxylic acid and glucosamine for the selection agent to be toxic to the strain, wherein the second selection agent differs from the first selection agent; and
    repeating the growing, selecting and measuring acts to obtain a second spontaneous mutant strain having enhanced ethanol production characteristics in comparison to the first obtained spontanerous mutant strain.

2. The method of claim 1 wherein the first selection agent is oxythiamine.

3. The method of claim 1 wherein the first selection agent is trehalose.

4. The method of claim 1 wherein the first selection agent is bromopyruvate.

5. The method of claim 1 wherein the first selection agent is glyoxylic acid.

6. The method of claim 1 wherein the first selection agent is glucosamine.

7. The method of claim 1 wherein the enhanced ethanol producing characteristic is at least one of: increased ethanol production measured as wt ethanol produced per volume, increased ethanol productivity measured as wt ethanol produced per volume per unit time, increased ethanol yield defined by wt ethanol produced per wt sugar fed to the strain, and increased specific ethanol productivity defined by wt ethanol produced per weight *S. cerevisiae* biomass per unit time.

8. A method of making a *S. cerevisiae* strain with enhanced ethanol producing characteristics comprising,
    contacting a culture of a parent strain of *S. cerevisiae* with a sufficient amount of a first selection agent selected from the group consisting of oxythiamine, trehalose, glyoxylic acid and glucosamine for the selection agent to be toxic to the parent strain;
    growing the contacted culture on a plating medium containing a sugar as a carbon source;
    selecting candidate spontaneous mutant strains of the culture that grow on the plating medium, and
    measuring an ethanol producing characteristic of the candidate spontaneous mutant strains to determine whether the candidate strain demonstrates enhanced ethanol production characteristics in comparison to the parent strain and if so, obtaining the *S. cerevisiae* strain with enhanced ethanol producing characteristics.

9. The method of claim 8 wherein the first selection agent is oxythiamine.

10. The method of claim 8 wherein the first selection agent is trehalose.

11. The method of claim 8 wherein the first selection agent is glyoxylic acid.

12. The method of claim 8 wherein the first selection agent is glucosamine.

13. The method of claim 8 wherein the obtained spontaneous mutant strain with enhanced ethanol production characteristics is contacted with an amount of a second selection agent selected from the group consisting of oxythiamine, trehalose, glyoxylic acid and glucosamine for the selection agent to be toxic to the strain, wherein the second selection agent differs from the first selection agent; and repeating the growing, selecting and measuring acts to obtain a second spontaneous mutant strain having enhanced ethanol production characteristics in comparison to the first obtained spontanerous mutant strain.

* * * * *